United States Patent [19]  [11] 3,993,778
Keck et al.  [45] Nov. 23, 1976

[54] ANTI-ULCEROGENIC PHARMACEUTICAL COMPOSITIONS CONTAINING A 2-AMINO-3,5-DIBROMO-BENZYLAMINE AND METHOD OF USE

[75] Inventors: Johannes Keck; Matyas Leitold; Sigfrid Puschmann; Gerd Kruger, all of Biberach an der Riss, Germany

[73] Assignee: Boehringer Ingelheim GmbH, Ingelheim am Rhein, Germany

[22] Filed: Mar. 25, 1975

[21] Appl. No.: 561,860

[30] Foreign Application Priority Data
Apr. 3, 1974  Germany............................ 2416142

[52] U.S. Cl. .............................................. 424/330
[51] Int. Cl.² ...................................... A61K 31/135
[58] Field of Search .................................... 424/330

[56] References Cited
UNITED STATES PATENTS
3,536,713  10/1970  Keck et al........................... 424/330

Primary Examiner—Frederick E. Waddell
Attorney, Agent, or Firm—Hammond & Littell

[57] ABSTRACT

Pharmaceutical compositions containing as an active ingredient an N-(hydroxy-cyclohexyl)-benzylamine of the formula

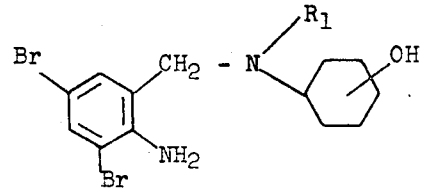

wherein $R_1$ is hydrogen or methyl, or a non-toxic, pharmacologically acceptable acid addition salt thereof; and a method of using the same as anti-ulcerogenics.

2 Claims, No Drawings

ANTI-ULCEROGENIC PHARMACEUTICAL COMPOSITIONS CONTAINING A 2-AMINO-3,5-DIBROMO-BENZYLAMINE AND METHOD OF USE

This invention relates to novel anti-ulcerogenic pharmaceutical compositions containing certain N-(hydroxycyclohexyl)-benzylamines, and to methods of using the same to inhibit the formation of stomach ulcers in warm-blooded animals.

More particularly, the present invention relates to novel anti-ulcerogenic pharmaceutical dosage unit compositions containing as an active ingredient an N-(hydroxy-cyclohexyl)-benzylamine of the formula

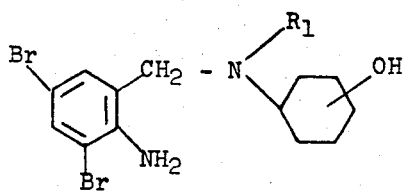

wherein $R_1$ is hydrogen or methyl, or a non-toxic, pharmacologically acceptable acid addition salt thereof.

The compounds embraced by formula I and their non-toxic, pharmacologically acceptable acid addition salts as well as various methods of preparing these compounds, are disclosed in U.S. Pat. No. 3,536,713. That patent also discloses that, within a single oral dosage unit range of 0.016 to 0.85 mgm/kg, preferably 0.065 to 0.35 mgm/kg, the compounds and their salts are effective antipyretics, secretolytics and antitussives.

We have now discovered that, within a substantially higher oral dosage unit range, namely 0.5 to 1.67 mgm/kg, these same compounds and their non-toxic acid addition salts are effective anti-ulcerogenics in warm-blooded animals, such as rats.

The anti-ulcerogenic activity of the compounds of the formula I and their non-toxic acid addition salts, that is, their ability to inhibit formation of stomach ulcers, was ascertained by the method described below, and the following are the results obtained for a representative species of the genus, namely, A = 3,5-dibromo-2-amino-N-(trans-4-hydroxy-cyclohexyl)-benzylamine hydrochloride.

The standard pharmacological test method of K. Tagaki et al, Jap. J. Pharmac. 19, 418 (1969), is used. The abdominal cavity of female rats having a body weight of 200 to 350 gm under ether anesthesia was opened, and the stomach was exposed. Thereafter, 0.05 ml of an aqueous 5% solution of acetic acid was injected in one location between the muscularis mucosae and the submucosa of the stomach of each animal, and the abdominal cavity was closed again. 3 to 5 days after this injection the animals developed stomach ulcers in the mucous membrane at the locus of injection, whereupon the animals were treated over a period of 3 weeks by adding the test compound at dosage levels of 50 and 100 mgm/kg to their daily food ration, using 5 to 8 animals per dose. The controls received only pulverized rat food. After 3 weeks, the animals were sacrificed, their stomachs were excised, and the size of the ulcer was determined by measuring its length and width. The anti-ulcerogenic effect of the test compound was expressed in terms of average percent difference in size of the treated ulcers over the controls (100%).

The following table shows the results obtained from these tests:

TABLE

| Compound | Dose in mgm/kg p.o. | % Reduction in ulcer size over controls |
|---|---|---|
| Controls | powdered food | 0 |
| A | 50 | − 52 |
|  | 100 | − 68 |

For pharmaceutical purposes the compounds of the formula I or their non-toxic acid addition salts are administered to warm-blooded animals perorally as active ingredients in customary dosage unit compositions, that is, compositions in dosage unit form consisting essentially of an inert pharmaceutical carrier and one effective anti-ulcerogenic dosage unit of the active ingredient, such as tablets, coated pills, capsules, wafers, powders, solutions, suspensions, emulsions syrups and the like. The effective anti-ulcerogenic oral single dosage unit of the compounds is from 0.5 to 1.67 mgm/kg body weight, preferably 0.58 to 1.0 mgm/kg body weight. The daily dose rate, administered in three to four single doses, is from 1.5 to 6.7 mgm/kg body weight, preferably 1.75 to 4.0 mgm/kg body weight.

The following examples illustrate a few oral pharmaceutical dosage unit compositions comprising a compound of the present invention as an active ingredient and represent the best modes contemplated of putting the invention into practical use. The parts are parts by weight unless otherwise specified.

EXAMPLE 1

Tablets

The tablet composition is compounded from the following ingredients:

| | | |
|---|---|---|
| N-(trans-4-hydroxy-cyclohexyl)-N-methyl-3,5-dibromo-2-amino-benzylamine hydrochloride | 50.0 | parts |
| Sec. calcium phosphate, anhydrous | 120.0 | '' |
| Colloidal silicic acid | 10.0 | '' |
| Corn starch | 30.0 | '' |
| Polyvinylpyrrolidone | 5.0 | '' |
| Potato starch | 20.0 | '' |
| Maleic acid | 3.0 | '' |
| Magnesium stearate | 2.0 | '' |
| Total | 240.0 | parts |

Preparation

The benzylamine salt, the calcium phosphate, the colloidal silicic acid and the corn starch are intimately admixed with each other, the mixture is moistened with an ethanolic 10% solution of the polyvinylpyrrolidone containing the maleic acid, the moist mass is granulated through a 1.5 mm-mesh screen, and the granulate is dried at 45° C and again passed through the screen. The granulate is then admixed with the potato starch and the magnesium stearate, and the resulting composition is compressed into 240 mgm-tablets in a conventional tablet making machine. Each tablet contains 50 mgm of the benzylamine salt and is an oral dosage unit composition with effective anti-ulcerogenic action.

EXAMPLE 2

Coated Pills

The pill core composition is compounded from the following ingredients:

| | | |
|---|---|---|
| 3,5-Dibromo-2-amino-N-(trans-4-hydroxy-cyclohexyl)-benzylamine hydrochloride | 50.0 | parts |
| Sec. calcium phosphate, anhydrous | 80.0 | " |
| Colloidal silicic acid | 10.0 | " |
| Corn starch | 20.0 | " |
| Polyvinylpyrrolidone | 5.0 | " |
| Potato starch | 10.0 | " |
| Maleic acid | 3.0 | " |
| Magnesium stearate | 2.0 | " |
| Total | 180.0 | parts |

Preparation

The ingredients are compounded as described in Example 1, and the composition is compressed into 180 mgm-pill cores which are subsequently coated with a thin shell consisting essentially of a mixture of sugar and talcum. Each coated pill contains 50 mgm of the benzylamine salt and is an oral dosage unit composition with effective anti-ulcerogenic action.

EXAMPLE 3

Gelatin Capsules

The capsule filler composition is compounded from the following ingredients:

| | | |
|---|---|---|
| N-Methyl-N-(cis-3-hydroxy-cyclohexyl)-3,5-dibromo-2-amino-benzylamine hydrochloride | 50.0 | parts |
| Potato starch | 40.0 | " |
| Talcum | 10.0 | " |
| Total | 100.0 | parts |

Preparation

The ingredients are intimately admixed with each other, and 100 mgm-portions of the mixture are filled into gelatin capsules of suitable size. Each capsule contains 50 mgm of the benzylamine salt and is an oral dosage unit composition with effective anti-ulcerogenic action.

EXAMPLE 4

Solution

The solution is compounded from the following ingredients:

| | | |
|---|---|---|
| 3,5-Dibromo-2-amino-N-(trans-2-hydroxy-cyclohexyl)-benzylamine hydrochloride | 0.5 | parts |
| Sugar | 70.0 | " |
| Tartaric acid | 0.3 | " |
| Sec. sodium phosphate . 2 H$_2$O | 1.2 | " |
| Saccharin sodium | 0.2 | " |
| Methyl p-hydroxy-benzoate | 0.07 | " |
| Propyl p-hydroxy-benzoate | 0.03 | " |
| Essence of eucalyptus-menthol | 0.1 | " |
| Raspberry flavoring | 0.02 | " |
| Ethanol, pure | 2.0 | " |
| Distilled water  q.s.ad | 100.0 | " |
| | | by vol. |

Preparation

About 50 ml of distilled water are heated to 80° C, and the p-hydroxybenzoates, the sugar, the saccharin sodium, the tartaric acid, the secondary sodium phosphate and the benzylamine salt are dissolved therein. Then, a solution of the essence of eucalyptus-menthol and the raspberry flavoring in the ethanol is stirred in. Subsequently the solution is diluted with distilled water to the indicated volume and filtered until clear. 10 ml of the solution contain 50 mgm of the benzylamine salt and are an oral dosage unit composition with effective anti-ulcerogenic action.

Analogous results are obtained when any one of the other benzylamines embraced by formula I or non-toxic, pharmacologically acceptable acid addition salt thereof is substituted for the particular benzylamine salt in Examples 1 through 4. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. The method of inhibiting the formation of stomach ulcers in a warm-blooded animal in need of such treatment, which comprises orally administering to said animal an effective anti-ulcerogenic amount of a compound of the formula $$\text{Br} - \underset{\underset{\text{Br}}{|}}{\underset{\text{NH}_2}{\bigcirc}} - CH_2 - N\underset{R_1}{\overset{}{\diagdown}} - \bigcirc - OH$$

wherein R$_1$ is hydrogen or methyl, or a non-toxic, pharmacologically acceptable acid addition salt thereof.

2. The method of claim 1, wherein said compound is N-(trans-4-hydroxy-cyclohexyl)-2-amino-3,5-dibromo-benzylamine or a non-toxic, pharmacologically acceptable acid addition salt thereof.

* * * * *